US005817683A

United States Patent [19]
Elliott et al.

[11] Patent Number: 5,817,683
[45] Date of Patent: Oct. 6, 1998

[54] ENDOTHELIN RECEPTOR ANTAGONISTS

[75] Inventors: John Duncan Elliott; Jia-Ning Xiang, both of Wayne, Pa.

[73] Assignee: SmithKline Beecham Corporation, Philadelphia, Pa.

[21] Appl. No.: 591,516

[22] Filed: Apr. 8, 1996

Related U.S. Application Data

[63] Continuation of Ser. No. 269,231, Jun. 29, 1994, abandoned, which is a continuation-in-part of Ser. No. 103,495, Aug. 6, 1993, abandoned.

[51] Int. Cl.$^6$ ........................ A01N 43/64; C07D 257/00; C07D 317/08
[52] U.S. Cl. .......................... 514/381; 514/382; 514/470; 548/252; 549/230
[58] Field of Search ........................... 548/252; 549/230; 514/381, 382, 470

[56] References Cited

U.S. PATENT DOCUMENTS

| | | | |
|---|---|---|---|
| 3,562,257 | 2/1971 | Kugita et al. | 260/239.3 |
| 5,102,999 | 4/1992 | Giordano et al. | 540/491 |

FOREIGN PATENT DOCUMENTS

| | | |
|---|---|---|
| 9015056 | 12/1990 | WIPO . |
| WO 93/08799 | 5/1993 | WIPO . |

OTHER PUBLICATIONS

Gupta et al, "Reaction of Benzyltriphenylarsonium Ylides . . . ", Indian Journal of Chemistry, vol. 24, Sect. B, Jul. 1985, pp. 783–784.
Gupta et al., "Reactions of Benzylpyridinium . . . ", Chemical Abstract, vol. 104 (1986), p. 671, Abs #129586r.
Gupta et al., "Reaction of Benzyltriphenylarsonium . . . ", Chemical Abstract, vol. 105 (1986), p. 601, Abs #97131r.
Dimroth et al., "Naphthalene, Phenanthrene, . . . ", Chemical Abstract, vol. 62 (1965), Col. 496, Paragraph b.
Atwal, "Tetrahydronaphthalenols for the Treatment of Hypertension", CA, vol. 104, Abs #148570.
Kerrigan, "Preparation . . . Dopaminergic Receptor Antagonists", CA, vol. 123, Abs #340154.
"The Merck Index", 1989—Merck & Co., Inc., Rahway, N.Y., U.S.A. XP002004174, p. 1008, Index–No. 6289, p. 1453, Index No. 9152.
Database Crossfire, Beilstein Informationssysteme GmBbH, Frankfurt, DE, XP002004175, *BRN=5573766* & Indian J. Chem. Sec. B., vol. 24, pp. 783–784 (1985).
Database Crossfire, Beilstein Informationssysteme GmBbH, Frankfurt, DE, XP002004176, *BRN=2596968* & Justus Liebigs Annalen Der Chemie, vol. 678, Weinheim DE, pp. 202–213 (1964).
Database Crossfire, Beilstein Informationssysteme GmBbH, Frankfurt, DE, XP002004177, *BRN=5577370* & Indian J. Chem. Sec. B., vol. 24, pp. 783–784 (1985).
Database Crossfire, Beilstein Informationssysteme GmBbH, Frankfurt, DE, XP002004178, *BRN=5577997* & Indian J. Chem. Sec. B., vol. 24, pp. 783–784 (1985).

*Primary Examiner*—Mukund J. Shah
*Assistant Examiner*—Tamthom T. Ngo
*Attorney, Agent, or Firm*—Linda E. Hall; Stephen A. Venetianer

[57] ABSTRACT

Naphthoic derivatives of the Formula (I)

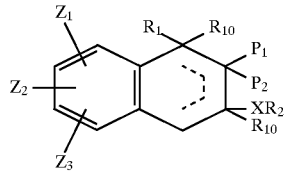

wherein the variables are defined herein; and pharmaceutical compositions containing these compounds, and their use as endothelin receptor antagonists are disclosed.

7 Claims, No Drawings

ENDOTHELIN RECEPTOR ANTAGONISTS

This is a 371 application of PCT/U.S. 94/08917 filed on Aug. 3, 1994 which is a continuation of Ser. No. 8/209,231 filed on Jun. 29, 1994, now abandoned; which is a cip of Ser. No. 8/103,495 filed on Aug. 6, 1993 now abandoned.

FIELD OF INVENTION

The present invention relates to novel compounds, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258:408-C415, 1990) and atherosclerosis, (Nakaki et al., Biochem. & Biophys. Res. Commun. 158: 880–881, 1989, and Lerman et al., New Eng. J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including human bronchus (Uchida et al., Eur J. of Pharm. 154: 227–228 1988, LaGente, Clin. Exp. Allergy 20: 343–348, 1990; and Springall et al., Lancet, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damage in the gastric mucosa (Whittle et al., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, Feb. 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidney Int, 37: 1487–1491, 1990) and endotoxin shock and other endotoxin induced diseases (Biochem. Biophys. Res. Commun., 161: 1220–1227, 1989, Acta Physiol. Scand. 137: 317–318, 1989) and inflammatory skin diseases. (Clin Res. 41:451 and 484, 1993).

Endothelin has also been implicated in preclampsia of pregnancy. Clark et al., Am. J. Obstet. Gynecol. March 1992, p. 962–968; Kamor et al., N. Eng. J. of Med., Nov. 22, 1990, p. 1486–1487; Dekker et al., Eur J. Ob. and Gyn. and Rep. Bio, 40 (1991) 215–220; Schiff et al., Am. J. Ostet. Gynecol. February 1992, p. 624–628; diabetes mellitus, Takahashi et al., Diabetologia (1990) 33:306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al, Endocrinology, Vol. 131, p. 603–607.

Endothelin has been reported to stimulate the transport of sperm in the uterine cavity, Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6:287–292 and Tejada et al., J. Amer. Physio. Soc. 1991, H1078–H1085.

Thus, endothelin receptor antagonists would offer a unique approach toward the pharmacotherapy of hypertension, renal failure, cerebrovascular disease, myocardial ischemia, angina, heart failure, asthma, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, preclampsia of pregnancy, bone remodeling, kidney transplant, male contraceptives, infertility and priaprism.

SUMMARY OF THE INVENTION

This invention comprises novel compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, heart failure, atherosclerosis, and as an adjunct in angioplasty for prevention of restenosis.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I):

1) A compound of Formula (I),

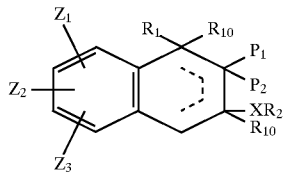

wherein:

$R_1$ is —$X(CH_2)_nAr$ or —$X(CH_2)_nR_8$ or

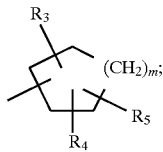 (c)

$R_2$ is hydrogen, Ar or (c);
$P_1$ is —$X(CH_2)_nR_8$;
$P_2$ is —$X(CH_2)_nR_8$, or —$XR_9Y$;
$R_3$ and $R_5$ are independently hydrogen, $R_{11}$, OH, $C_{1-8}$alkoxy, —$S(O)_qR_{11}$, —$N(R_6)_2$, Br, F, I, Cl, $CF_3$, —$NHCOR_6$, —$R_{11}CO_2R_7$, —$R_{11}CO_2R_7$, —$XR_9$—Y or —$X(CH_2)_nR_8$ wherein each methylene group within —$X(CH_2)_nR_8$ may be unsubstituted or substituted by one or two —$(CH_2)_nAr$ groups;
$R_4$ is hydrogen, $R_{11}$, OH, $C_{1-5}$alkoxy, —$S(O)_qR_{11}$, —$N(R_6)_2$, —$X(R_{11})$, Br, F, I, Cl or —$NHCOR_6$ wherein the $C_{1-5}$alkoxy may be unsubstituted or substituted by OH, methoxy or halogen;
$R_6$ is independently hydrogen or $C_{1-4}$alkyl;
$R_7$ is independently hydrogen, $C_{1-10}$alkyl, $C_{2-10}$alkenyl or $C_{2-8}$ alkynyl, all of which may be unsubstituted or substituted by one or more OH, —$N(R_6)_2$, —$CO_2R_{12}$, halogen or $XC_{1-5}$ alkyl; or $R_7$ is $(CH_2)_nAr$;
$R_8$ is hydrogen, $R_{11}$, —$CO_2R_7$, —$CO_2C(R_7)_2O(CO)XR_{11}$, $PO_3(R_7)_2$, —$SO_2NR_7R_{11}$, —$CONR_7SO_2R_{11}$, —$SO_3R_7$, —$SO_2R_7$, —$P(O)(OR_7)R_7$, CN, —$C(O)N(R_6)_2$, —$NR_7SO_2R_{11}$, tetrazole or $OR_6$;
$R_9$ is $(CH_2)_n$, $C_{1-10}$alkyl, $C_{2-10}$alkenyl or phenyl all of which may be unsubstituted or substituted by one or more OH, $N(R_6)_2$, COOH, halogen, >C=O or $XC_{1-5}$alkyl;
$R_{10}$ is $R_3$ or $R_4$;
$R_{11}$ is Ar, $C_{3-8}$cycloalkyl, $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;
$R_{12}$ is hydrogen, $C_{1-6}$alkyl, $C_{2-6}$alkenyl or $C_{2-7}$alkynyl;
X is $(CH_2)_n$, O, $NR_6$ or $S(O)_q$;
Y is $CH_3$ or $X(CH_2)_nAr$;

Ar is:

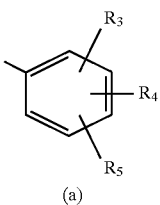 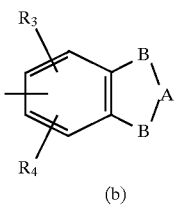
(a) (b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;
A is C=O, or $[C(R_6)_2]_m$;
B is —$CH_2$— or —O—;
$Z_1$ and $Z_2$ are independently hydrogen, $C_{1-8}$alkyl, $C_{2-8}$alkenyl, $C_{2-8}$alkynyl, OH, $C_{1-8}$alkoxy, $S(O)qC_{1-8}$alkyl, $N(R_6)_2$, Br, F, I, Cl, $NHCOR_6$, —$X(CH_2)_nR_8$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, $CO(CH_2)_nCH_3$, $CO(CH_2)_nCH_2N(R_6)_2$, or halogen; or $Z_1$ and $Z_2$ together may be —O—A—O— on contiguous carbons;
$Z_3$ is $Z_1$ or $XR_9Y$;
q is zero, one or two;
n is an integer from 0 to six;
m is 1, 2 or 3; and the dotted line indicates the optional presence of one or two double bonds; or a pharmaceutically acceptable salt thereof; provided that:
$R_2$ is not hydrogen when X is $S(O)_q$;
when an optional double bond is present there is only one $R_{10}$, and when the double bond is adjacent to $P_1$ and $P_2$, there is no $P_1$ and $P_2$ is not $NR_6R_9Y$;
when an optional double bond is present in Formula (I) and X—$R_2$ is attached to the double bond, X is not $NR_6$;
when an optional double bond is present and $R_1$ is attached directly to the double bond, $R_1$ is not $NR_6Ar$;
when $R_3$, $R_5$, $Z_1$, $Z_2$, or $Z_3$ is $X(CH_2)_nR_8$ and n is 0, X is not oxygen or $NR_6$ when $R_8$ is $OR_6$ or $CO_2H$;
when $R_8$ is $CO(CR_{11})_2O(CO)XR_7$, X is not $S(O)_q$;
when there are two double bonds present and $R_1$ and $R_2$ are phenyl, $R_3$, $R_4$ and $R_5$ are not all hydrogen.

Also included in the invention are pharmaceutically acceptable salt complexes.

All alkyl, alkenyl, alkynyl and alkoxy groups may be straight or branched. The term "halogen" is used to mean iodo, fluoro, chloro or bromo.

The compounds of the present invention may contain one or more asymmetric carbon atoms and may exist in racemic and optically active form. All of these compounds and diastereoisomers are contemplated to be within the scope of the present invention.

Preferred compounds are those wherein $R_1$ is $X(CH_2)_nAr$, (Ar is (a) or (b)), dihydrobenzofuranyl, benzodioxanyl, cyclohexyl, $C_{1-4}$alkyl; $R_2$ is (a), (b) $C_{1-4}$alkyl, indolyl or hydrogen; $R_3$ and $R_5$ are independently hydrogen, OH, $C_{1-5}$alkoxy, halogen, —$OC_{1-4}$alkyl phenyl, $R_{11}CO_2R_7$, $C_{1-4}$alkyl, $N(R_6)_2$, $NH(CO)CH_3$, —$X(CH_2)_nR_8$, —$XR_9$ pyridyl, phenyl or $S(O)_pC_{1-5}$alkyl; $R_4$ is hydrogen, OH, $C_{1-5}$alkoxy, halogen, $C_{1-4}$alkyl, $N(R_6)_2$, $NH(CO)CH_3$ or $S(O)_pC_{1-5}$alkyl; $Z_1$, $Z_2$ and $Z_3$ are independently $XR_9Y$, benzyl, hydrogen, OH, $C_{1-5}$alkoxy, $—N(R_6)_2$, $S(O)qC_{1-8}$alkyl, $NHCOR_6$, $X(CH_2)_nR_8$ or halogen, or $Z_1$ and $Z_2$ together may be —O—A—O on contiguous carbons; $P_1$ and $P_2$ are independently hydrogen, $CO_2H$ or tetrazole, Ar is (a), (b), phenyl, or pyridyl; X is $(CH_2)_n$ or oxygen.

More preferred are compounds wherein $R_3$ is hydrogen or $—X(CH_2)_nR_8$, $R_{11}CO_2R_7$; $R_4$ and $R_5$ are independently hydrogen, OH, $C_{1-5}$alkoxy, $SC_{1-5}$alkyl, F, Br, $C_{1-3}$alkyl or $NH_2$; $Z_1$ and $Z_3$ are hydrogen and $Z_2$ is hydrogen, OH, $C_{1-5}$alkoxy, halogen, $X(CH_2)_nR_8$, $NH_2$, benzyl, NH(CO)$CH_3$, or $Z_1$ and $Z_2$ together may be O—A—O.

Most preferred are compounds wherein $R_1$ is (a) or (b) and $R_2$ is (a) or (b); A is $CH_2$, B is —O—; there is no optional double bond; $R_1$ and $XR_2$ are trans to $P_1$; $Z_2$ is OH, $C_{1-5}$alkoxy, $—OCH_2CHCH_2$ or hydrogen, $Z_1$ and $Z_3$ are hydrogen; $R_3$ is XAr, hydrogen, $X(CH_2)_q$COOH, $X(CH_2)_q$CONR$_7$SO$_2$R$_{11}$ or $CH=CHCO_2H$, $R_4$ is hydrogen, substituted phenyl, or $C_{1-2}$alkoxy; and $R_5$, $R_{10}$ and $P_2$ are hydrogen.

The present invention provides Compounds of Formula (I)

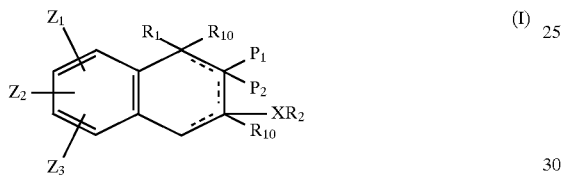

(I)

which for compounds wherein X is $(CH_2)_n$, n is 0 and $R_{10}$ is H, can be prepared by a process which comprises:

a) reacting a substituted aldehyde of Formula (2)

$R_2CHO$ (2)

with dimethyl malonate in a suitable solvent such as benzene with a catalyst such as piperidinium acetate at reflux to provide a compound of Formula (3).

(3)

Reaction of a compound of Formula (3) with a benzylsilane of structure (4) (wherein Y is $C_{1-5}$alkyl)

(4)

in the presence of anhydrous cesium fluoride in a solvent such as HMPA at 40°–100° C. affords compounds of structure (5).

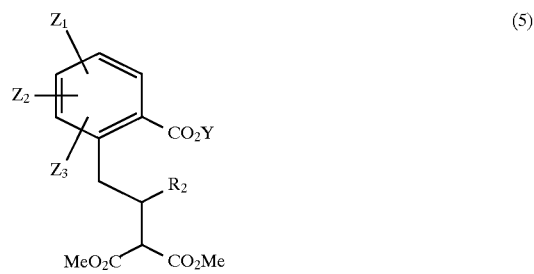

(5)

Benzylsilanes of Formula (4) may be prepared from the corresponding orthomethyl benzoic acid esters (6) by treatment with a base such as lithium di-isopropylamide in the presence of chlorotrimethylsilane in a solvent such as anhydrous ether.

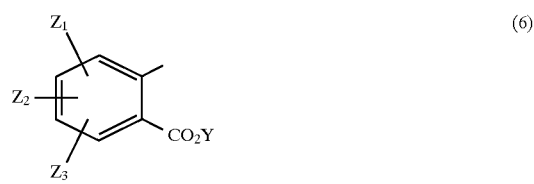

(6)

Saponification of a compound of Formula (5) using aqueous sodium or potassium hydroxide in a suitable solvent such as methanol or isopropanol followed by acidification with a dilute mineral acid such as hydrochloric affords a tri-acid of structure (7).

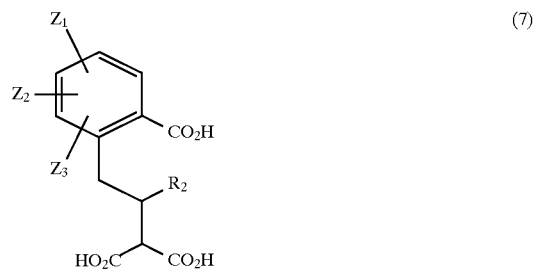

(7)

Thermolysis of a compound of Formula (7) at between 150°–250° C. affords a di-acid of Formula (8).

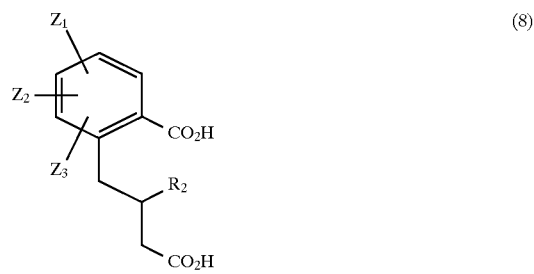

(8)

Re-esterification of a compound of structure (8) with diazomethane in a solvent such as ether or alternatively treatment of (8) with a base such as 1,8-diazabicyclo[5.4.0]undec-7-ene in a solvent such as acetonitrile followed by the addition of iodomethane affords diesters of Formula (9). As a further alternative, compounds of structure (9) may be prepared from (8) by treatment with methanolic hydrogen chloride.

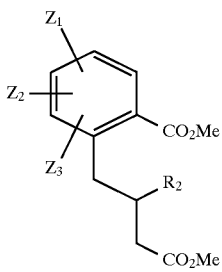

(9)

Dieckmann cyclization of a di-ester of formula (9) using sodium methoxide in methanol as a solvent affords, after acidic work-up, a β-keto-ester of Formula (10).

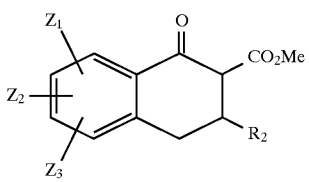

(10)

Treatment of a compound of Formula (10) with diazomethane in a solvent such as ether affords enol ethers of Formula (11).

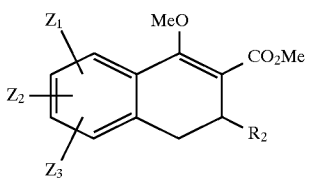

(11)

Reaction of a compound of Formula (11) with a Grignard reagent of Formula (12).

(12)

wherein $R_1$ is $X(CH_2)_n Ar$, and X is $(CH_2)_n$ in a solvent such as ether or ether/tetrahydrofuran at approximately 0° C. affords compounds of Formula (13).

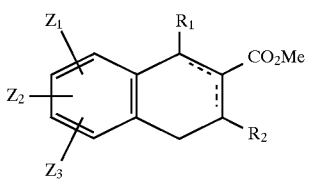

(13)

Hydrogenation of a compound of Formula (13) under hydrogen gas at approximately 50 p.s.i. in a suitable solvent such as ethyl acetate in the presence of a suitable catalyst such as 5–10% palladium on charcoal affords a racemic compound of Formula (14) with the predominant relative stereochemistry shown.

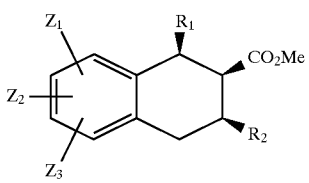

(14)

Epimerization using a base such as potassium t-butoxide in a solvent such as tertiary butanol affords a compound of Formula (15).

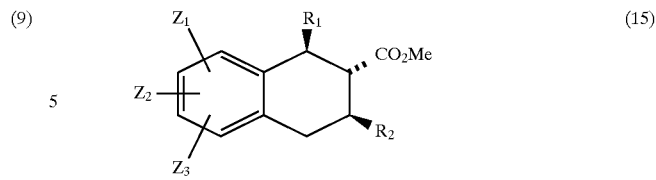

(15)

Saponification of an ester of Formula (15) using aqueous sodium or potassium hydroxide in a suitable solvent such as methanol or isopropanol affords, after acidification with a dilute mineral acid such as hydrochloric, an acid of Formula (16).

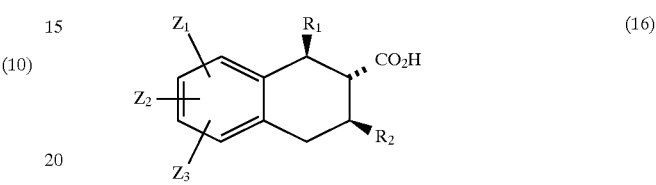

(16)

b) As an alternative, treatment of a β-keto-ester of Formula (10) with a base such as sodium hydride in a solvent such as tetrahydrofuran followed by the addition of N-phenyltrifluoromethanesulfonimide affords compounds of Formula (17).

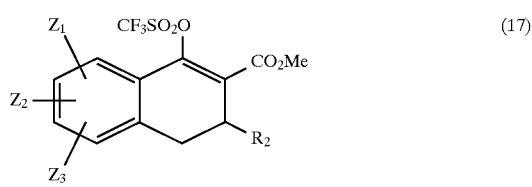

(17)

An enol triflate of Formula (17) may also be prepared from a compound of structure (10) by treatment with a base such as N,N-di-isopropylethylamine in a solvent such as dichloromethane followed by trifluoromethanesulfonic anhydride. Treatment of an enol triflate of Formula (17) with an organostannane of Formula (18)

(18)

wherein $R_1$ is Ar in a solvent such as dioxane in the presence of a catalyst such as tetrakis(triphenylphosphine)palladium (0) affords compounds of Formula (19).

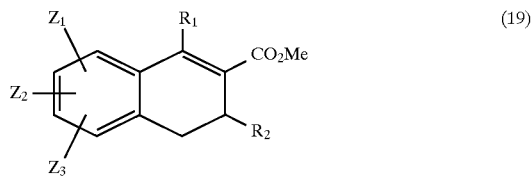

(19)

Hydrogenation of a compound of structure (19) as described above for compounds of Formula (13) affords tetrahydronaphthalenes of Formula (14).

c) As a further alternative treatment of a β-keto-ester of Formula (10) with an organocerium reagent of Formula (20)

(20)

in a solvent such as tetrahydrofuran at −78° C. affords a product of Formula (21). Organocerium compounds of Formula (20) may be prepared by treatment of the corresponding orgnolithium compound with anhydrous cerium III chloride at −78° C. in a solvent such as tetrahydrofuran.

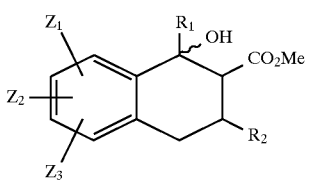

(21)

Hydrogenation of compounds of Formula (21) under hydrogen gas at approximately 50 p.s.i. in a suitable solvent such as ethyl acetate containing 5–20% acetic acid in the presence of a suitable catalyst such as 5–10% palladium on charcoal affords, after saponification as described for compounds of Formula (15), tetrahydronaphthalene carboxyclic acids of Formula (16).

d) Saponification of esters of type (13) using aqueous sodium or potassium hydroxide in a suitable solvent such as methanol or isopropanol affords, after acidification with a dilute mineral acid such as hydrochloric, acids of Formula (21), the double bond isomers of which may be separated chromatographically.

With appropriate manipulation and protection of any chemical functionalities, synthesis of the remaining compounds of the Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) Membrane Preparation

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000×g for 10 minutes at 4° C. The supernatant was removed and centrifuged at 40,000×g for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 mg of membrane protein was used for each tube in binding experiments.

B) [$^{125}$I]ET-1 Binding Protocol

[$^{125}$I]ET-1 binding to membranes from rat cerebellum (2–5 mg protein/assay tube) or kidney cortex (3–8 mg protein/assay tube) were measured after 60 minutes incubation at 30° C. in 50 mM Tris HCl, 10 mM $MgCl_2$, 0.05%

BSA, pH 7.5 buffer in a total volume of 100 ml. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$/ 5% $CO_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean±S.E.M. Dissociation constants ($K_b$) of competitive antagonists were determined by the standard method of Arunlakshana and Schild.

The following examples are illustrative and are not limiting of the compounds of this invention.

EXAMPLE 1

(1RS, 2SR, 3SR)-1,3-Bis(3,4-methylene-dioxyphenyl)-1,2,3,4-tetrahydro-2-naphthoic Acid a) Benzyl-methyl-2-[1-(3,4-methylenedioxyphenyl)-2-(2-methylcarboxyphenyl)ethyl] malonate To a solution of benzyl, methyl-2-(3,4-methylenedioxybenzyliden)-malonate (2.16 g, 6.35 mmol) and methyl o-trimethylsilylmethyl benzoate (2.12 g, 9.53 mmol) in HMPA (6 mL) at room temperature was added CsF (1.93 g, 12.70 mmol) in one portion. The mixture was heated to 60° C. for 3 h under argon and then quenched with water, and extracted with 1:1 EtOAc/Hexane. The organic layer was separated and washed with brine and dried ($NaSO_4$). After removing the solvent, chromatography of the residue with 4:1 Hexane/EtOAc gave 1.87 g (60%) of an inseparable 1:1 mixture of title compounds as colorless oil: Rf 0.31 (silica gel, 2:1 n-hexane/EtOAc).

b) Methyl-3-(3,4-methylenedioxyphenyl)-4-(2-methylcarboxyphenyl)butanoate

To a solution of triester (a) (3.30 g, 6.73 mmol) in 10 mL of ether acetate was added 330 mg of 10% Pd/C and the mixture was stirred under $H_2$ atmosphere at room temperature for 7 h. Filtration and concentration gave 2.70 g of the crude acids which were directly used in the following reaction without further purification.

The neat crude acids (2.70 g) were heated to 150° C. for 1 h and flash chromatography of the residue with 4:1 n-hexane/ethyl acetate gave 2.30 g (96% over two steps) of (b) as a colorless oil: Rf 0.46 (silica gel, 2:1 n-hexane/EtOAc).

c) (±)-Phenethyl—(3SR)-1-methoxy-3-(3,4-methylenedioxyphenyl)-3,4-dihydro-2-naphthoate To a solution of diester (800 mg, 2.24 mmol) in 10 mL of THF was added 3 mL of a solution of 25% wt NaOMe/MeOH and the mixture was heated to reflux for 1 h. After cooling to room temperature, the mixture was poured into 1N HCl and extracted twice with 1:1 hexane/EtOAc. The combined oraginc extract was washed with brine and dried ($Na_2SO_4$). Removal of the solvent gave the crude b-keto ester, which was used in the next reaction without further purification.

To a solution of the crude b-keto ester in 10 mL of toluene was added phenethyl alcohol (0.41 mL, 3.36 mmol) and DMAP (10 mg) and the mixture was refluxed for 28 h. After cooling to room temperature, the mixture was poured into water and extracted twice with 1:1 hexane/EtOAc. The combined oraginc extract was washed with brine and dried ($Na_2SO_4$). Removal of the solvent gave the crude b-keto ester, which was used in the next reaction without further purification.

To a solution of the crude ester in 10 mL of ethanol at room temperature was added 20 mL of diazomethane solution (13 mmol) and the mixture was stirred under argon at room temperature for 17 h. The reaction was quenched with AcOH and the solution was then concentrated. Flash chromatography of the residue with 4:1 hexane/EtOAc gave 647 mg (67% over 3 steps) of a 1:1 mixture of inseparable diastereomeric methyl enoethers (c) as colorless oil.

d) (+)-Phenethyl—(3SR)-1,3-bis(3,4-methylenedioxyphenyl)-3,4-dihydro-2-naphthoate To a mixture of 1-bromo-3,4-methylenedoxybenzene (423 mg, 2.10 mmol) and Mg (68 mg, 2.80 mmol) in 3 mL of THF was added 2 uL of MeI and the mixture was irradiated by ultrasound for 30 min. (Mg disappeared). To a solution of methyl enol ether 7 (300 mg, 0.70 mmol) in 4 mL of THF at 0° C. under argon was dropwise added the grinard reagent methylenedioxyphenyl MgBr in THF. After 15 minute, the reaction was quenched with aq. HCl and the mixture was extracted with 1:1 hexane/EtOAc. The organic extract was washed with brine and dried ($Na_2SO_4$). After removing the solvent, flash chromatography of the residue with 4:1 hexane/EtOAc gave 250 mg (69%) of 1:1 mixture of inseparable diastereomers (d) as colorless oil: Rf 0.45 (silica gel, 3:1 n-hexane/EtOAc); MS m/e ($MH^+$) 519; Anal. Calcd. for $C_{33}H_{26}O_6$: C, 76.43; H, 5.05. Found: C, 76.70; H, 5.14.

e) (1RS, 2SR, 3SR)-Methyl-1,3-bis(3,4-methylenedioxyphenyl)-1,2,3,4-tetrahydro-2-naphthoate To a solution of phenethylester (d) (454 mg, 0.876 mmol) in 4 mL of EtOAc was added 60 mg of 10% Pd/C and shaken under $H_2$ (55 Psi) at room temperature for 24 h. After filtration and concentration, the residue was dissolved in ether and added excess of diazomethane solution in ether. The reaction was quenched with acetic acid and washed with water, brine and dried ($Na_2SO_4$). After removing the solvent, flash chromatography of the residue with 4:1 Hexane/EtOAc gave 160 mg (43%) of methyl ester (e) as a colorless oil:Rf 0.52 (silica gel, 3:1 n-hexane/EtOAc).

f) (1RS, 2RS, 3SR)-Methyl-1,3-bis(3,4-methylenedioxyphenyl)-1,2,3,4-tetrahydro-2-naphthoate To solution of methyl ester (e) (160 mg, 0.373 mmol) in 3 mL of THF was added 0.7 mL of 25% NaOMe/MeOH and stirred at room temperature under argon for 18 h. The mixture was poured into 1N HCl and extracted with 1:1 Hexane/EtOAc. The organic extract was washed with brine and dried ($Na_2SO_4$). After removing the solvent, flash chromatography of the residue with 4:1 n-hexane/EtOAc gave 130 mg (81%) of (f) as a white solid: Rf 0.52 (silica gel, 3:1 n-hexane/EtOAc).

g) (1RS, 2SR, 3SR)-1,3-Bis(3,4-methylenedioxyphenyl)-1,2,3,4-tetrahydro-2-naphthoic Acid To a solution of methyl ester (f) (110 mg, 0.257 mmol) in 6 mL of 1:1 MeOH/THF was added 2 mL of 10% NaOH and heated to 70° C. for 7 h. The mixture was poured into water and washed with 1:1 Hexane/EtOAc. The aqeous solution was acidified with 6N HCl to pH 5 and extracted with EtOAc. The organic extract was washed eith brine and dried ($Na_2SO_4$). Removal of the solvent gave 100 mg (94%) of the title acid as a white solid: Rf 0.07 (silica gel, 2:1 n-hexane/EtOAc); $^1$H NMR ($CDCl_3$) d 3.00–3.25 (m, 3H), 4.38 (d, J=10.8 Hz, 1H), 5.94 (s, 4H), 6.55–7.18 (m, 10H); MS m/e 416 ($M^+$); FAB HRMS Calcd. for $C_{25}H_{19}O_6Na_2$:461.0977. Found: 461.0954. Anal. Calcd. for $C_{25}H_{19}O_6 \cdot H_2O$: C, 69.12; H, 5.10. Found: C, 68.89 H, 0.5.41

EXAMPLE 2

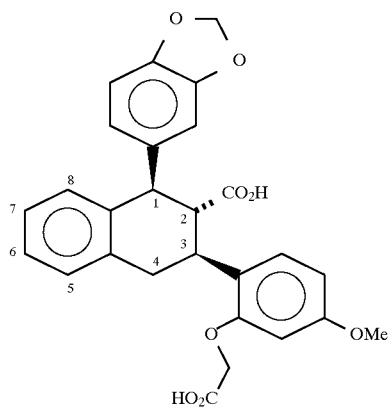

(1RS, 2RS, 3SR)-3-(2-carboxymethoxy-4-methoxyphenyl)-1-(3,4-methylenedioxyphenyl)-1,2,3,4-tetrahydro-2-naphthoic Acid

EXAMPLE 3

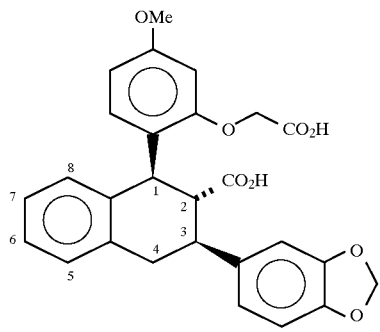

(IRS, 2SR, 3RS)-1-(2-Carboxymethoxy-4-methoxyphenyl)-3-(3,4-methylenedioxyphenyl)-1,2,3,4-tetrahydro-2-naphthoic Acid

EXAMPLE 4

Formulations for pharmaceutical use incorporating compounds of the present invention can be prepared in various forms and with numerous excipients. Examples of such formulations are given below.

Inhalant Formulation

A compound of Formula (I) (1 g) is aerosolized from a metered dose inhaler to deliver the desired amount of drug per use.

| Tablets/Ingredients | | Per Tablet |
|---|---|---|
| 1. | Active ingredient (Cpd of Form. (I)) | 40 mg |
| 2. | Corn Starch | 20 mg |
| 3. | Alginic acid | 20 mg |
| 4. | Sodium Alginate | 20 mg |
| 5. | Mg stearate | 1.3 mg |
| | | 2.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of Formula (I) in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of Formula (I),

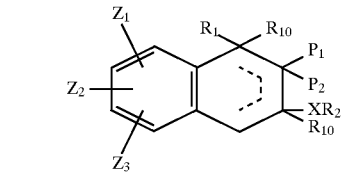

wherein:

$R_1$ is —$X(CH_2)_n Ar$ or $R_1$ is $C_{1-4}$ alkyl or cyclohexyl;

$R_2$ is Ar or (c)

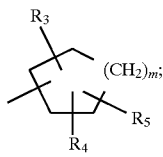

$P_1$ is $(CH_2)_nCOOR_7$, $-CONH_2$, or tetazole;

$P_2$ is hydrogen;

$R_3$ and $R_5$ are independently hydrogen, $R_{11}$, OH, $C_{1-8}$alkoxy, $-S(O)_qR_{11}$, $N(R_6)_2$, Br, F, I, Cl, $CF_3$, $-NHCOR_6$, $-R_{11}CO_2R_7$, $-R_{11}CO_2R_7$, $-XR_9-Y$ or $-X(CH_2)_nR_8$ wherein each methylene group within $-X(CH_2)_nR_8$ may be unsubstituted or substituted by one or two $-(CH_2)_nAr$ groups;

$R_4$ is independently hydrogen, $R_{11}$, OH, $C_{1-5}$alkoxy, $-S(O)_qR_{11}$, $-N(R_6)_2$, $-X(R_{11})$, Br, F, I, Cl or $-NHCOR_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen, $C_{1-10}$alkyl, $C_{2-10}$alkenyl or $C_{2-8}$ alkynyl, all of which may be unsubstituted or substituted by one or more OH, $-N(R_6)_2$, $-CO_2R_{12}$, halogen or $XC_{1-5}$ alkyl; or $R_7$ is $(CH_2)_nAr$;

$R_8$ is independently hydrogen, $R_{11}$, $-CO_2R_7$, $-CO_2C(R_7)_2O(CO)XR_{11}$, $PO_3(R_7)_2$, $-SO_2NR_7R_{11}$, $-CONR_7SO_2R_{11}$, $-SO_3R_7$, $-SO_2R_7$, $-P(O)(OR_7)R_7$, CN, $-C(O)N(R_6)_2$, $-NR_7SO_2R_{11}$, tetrazole or $OR_6$;

$R_9$ is independently $(CH_2)_n$, $C_{1-10}$alkyl, $C_{2-10}$alkenyl or phenyl all of which may be unsubstituted or substituted by one or more OH, $N(R_6)_2$, COOH, halogen, $>C=O$ or $XC_{1-5}$alkyl;

$R_{10}$ is hydrogen;

$R_{11}$ is independently Ar, $C_{3-8}$cycloalkyl, $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;

$R_{12}$ is hydrogen, $C_{1-6}$alkyl, $C_{2-6}$alkenyl or $C_{2-7}$alkynyl;

X is independently $(CH_2)_n$, O, $NR_6$ or $S(O)_q$;

Y is independently $CH_3$ or $X(CH_2)_nAr$;

Ar is independently:

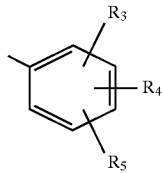

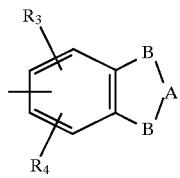

or naphthyl; all of which may be unsubstituted or substituted by one or more $R_3$ or $R_4$ groups;

A is independently $C=O$, or $(C(R_6)_2)_m$;

B is independently $-CH_2-$ or $-O-$;

$Z_1$ and $Z_2$ are independently hydrogen, $C_{1-8}$alkyl, $C_{2-8}$alkenyl, $C_{2-8}$alkynyl, OH, $C_{1-8}$alkoxy, S(O)q$C_{1-8}$alkyl, $N(R_6)_2$, Br, F, I Cl, $NHCOR_6$, $-X(CH_2)_nR_8$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, $CO(CH_2)_nCH_3$, $CO(CH_2)_nCH_2N(R_6)_2$, or halogen; or $Z_1$ and $Z_2$ together may be $-O-A-O-$ on contiguous carbons;

$Z_3$ is $Z_1$ or $XR_9Y$;

q is zero, one or two;

n is independently an integer from 0 to six;

m is 1, 2 or 3; and the dotted line indicates the optional presence of one or two double bonds; or a pharmaceutically acceptable salt thereof; provided that when an optional double bond is present there is only one $R_{10}$ and when the double bond is adjacent to $P_1$ and $P_2$, there is no $P_2$;

when an optional double bond is present in Formula (I) and $X-R_2$ is attached to the double bond, X is not $NR_6$;

when an optional double bond is present and $R_1$ is attached directly to the double bond, $R_1$ is not $NR_6Ar$;

when $R_3$, $R_5$, $Z_1$, $Z_2$, or $Z_3$ is $X(CH_2)_nR_8$ and n is 0, X in the $X(CH_2)_nR_8$ is not oxygen or $NR_6$ when $R_8$ is $OR_6$ or $CO_2H$; and when $R_8$ is $CO(CR_{11})_2O(CO)XR_7$, X is not $S(O)_q$; or when there are two double bonds present and $R_1$ and $R_2$ are phenyl; $R_3$, $R_4$ and $R_5$ are not all hydrogen.

2. A compound of claim 1 wherein $R_1$ is $X(CH_2)_nAr$, $R_2$ is (a) or (b); $R_3$ and $R_5$ are independently hydrogen, OH, $C_{1-5}$alkoxy, halogen, $-OC_{1-4}$alkyl phenyl, $R_{11}CO_2R_7$, $C_{1-4}$alkyl, $N(R_6)_2$, $NH(CO)CH_3$, $-X(CH_2)_nR_8$, phenyl or $S(O)_pC_{1-5}$alkyl; $R_4$ is hydrogen, OH, $C_{1-5}$alkoxy, halogen, $C_{1-4}$alkyl, $N(R_6)_2$, $NH(CO)CH_3$ or $S(O)_pC_{1-5}$alkyl; $Z_1$, $Z_2$ and $Z_3$ are independently $XR_9Y$, benzyl, hydrogen, OH, $C_{1-5}$alkoxy, $-N(R_6)_2$, S(O)q$C_{1-8}$alkyl, $NHCOR_6$, $X(CH_2)_nR_8$ or halogen, or $Z_1$ and $Z_2$ together may be $-O-A-O$ on contiguous carbons; $P_1$ is $CO_2H$ or tetrazole; X is $(CH_2)_n$ or oxygen.

3. A compound of claim 2 wherein $R_3$ is hydrogen or $-X(CH_2)_nR_8$, $R_{11}CO_2R_7$; $R_4$ and $R_5$ are independently hydrogen, OH, $C_{1-5}$alkoxy, $SC_{1-5}$alkyl, F, Br, $C_{1-3}$alkyl or $NH_2$; $Z_1$ and $Z_3$ are hydrogen and $Z_2$ is hydrogen, OH, $C_{1-5}$alkoxy, halogen, $X(CH_2)_nR_8$, $NH_2$, benzyl, $NH(CO)CH_3$, or $Z_1$ and $Z_2$ together may be $O-A-O$.

4. A compound of claim 3 wherein $R_1$ is (a) or (b); $R_2$ is (a) or (b); A is $CH_2$, B is $-O-$; there is no optional double bond; $R_1$ and $XR_2$ are trans to $P_1$; $Z_2$ is OH, $C_{1-5}$alkoxy, $-OCH_2CHCH_2$ or hydrogen, $Z_1$ and $Z_3$ are hydrogen; $R_3$ is XAr, hydrogen, $X(CH_2)_qCOOH$, $X(CH_2)_qCONR_7SO_2R_{11}$ or $CH=CHCO_2H$, $R_4$ is hydrogen, substituted phenyl, or $C_{1-2}$alkoxy; and $R_5$ is hydrogen.

5. A pharmaceutical composition comprising a compound of claim 1 and a pharmaceutically acceptable carrier.

6. A method of antagonizing endothelin receptors which comprises administering to a subject in need thereof, an effective amount to antagonize endothelin receptors or a compound of claim 1.

7. A method of treating hypertension, renal failure or cerebrovascular disease which comprises administering to a subject in need thereof, an effective amount of a compound of claim 1.

* * * * *